United States Patent
Reichbach

(10) Patent No.: US 12,257,178 B2
(45) Date of Patent: Mar. 25, 2025

(54) SHEATH SHAPED BARRIER DEVICE WITH EXPANDABLE FEATURE

(71) Applicant: Abraham Reichbach, St. Pete Beach, FL (US)

(72) Inventor: Abraham Reichbach, St. Pete Beach, FL (US)

(73) Assignee: Abraham Reichbach, St. Pete Beach, FL (US)

( * ) Notice: Subject to any disclaimer, the term of this patent is extended or adjusted under 35 U.S.C. 154(b) by 501 days.

(21) Appl. No.: 17/306,440

(22) Filed: May 3, 2021

(65) Prior Publication Data

US 2022/0347006 A1    Nov. 3, 2022

(51) Int. Cl.
*A61F 6/04*    (2006.01)

(52) U.S. Cl.
CPC .................... *A61F 6/04* (2013.01)

(58) Field of Classification Search
CPC ........ A61F 6/04; A61F 5/41; A61F 2005/411; A61F 5/44; A61F 6/02; A61F 2006/043; A61F 2006/048; A61F 2005/417; A61F 2005/412; A61H 9/0057
USPC .................................. 128/844, 842
See application file for complete search history.

(56) References Cited

U.S. PATENT DOCUMENTS

| | | | |
|---|---|---|---|
| 5,113,599 A | 5/1992 | Cohen et al. | |
| 5,823,939 A * | 10/1998 | Tsagarakis | A61F 5/41 600/38 |
| 5,885,205 A | 3/1999 | Kassman | |
| 2007/0186935 A1 | 8/2007 | Wang et al. | |
| 2013/0090524 A1* | 4/2013 | McNamara | A61H 19/44 600/38 |
| 2020/0085612 A1* | 3/2020 | Clarke | A61F 5/41 |

FOREIGN PATENT DOCUMENTS

KR    200466449 Y1    4/2013

* cited by examiner

*Primary Examiner* — Alireza Nia
*Assistant Examiner* — Daniel A Miller
(74) *Attorney, Agent, or Firm* — Volpe Koenig

(57) ABSTRACT

A sheath shaped barrier device including an expandable feature is disclosed herein. The sheath shaped barrier device includes an elongated tube with a first end defining an enclosed tip and a second end defining an opening dimensioned to receive male genitalia. At least one sealed passage is defined along the elongated tube. A container is positioned proximal to the second end of elongated tube and in fluid communication with the at least one sealed passage. The container includes partitioned quantities of a liquid, citric acid, and sodium bicarbonate. The container is configured to rupture upon application of a predetermined force to allow the liquid, the citric acid, and the sodium bicarbonate to mix with each other upon the application of the predetermined force.

12 Claims, 3 Drawing Sheets

SHEATH SHAPED BARRIER DEVICE WITH EXPANDABLE FEATURE

FIELD OF INVENTION

The present disclosure relates to a sheath shaped barrier device, and is more particularly related to an expandable sheath shaped barrier device.

BACKGROUND

Sheath shaped barrier devices, i.e. condoms or prophylactics, typically include an elongated body formed from an elastic material, such as polyurethane. The primary purpose of these barrier devices is to prevent the transmission of sexually transmitted infections and also reduce the chance of pregnancy. Sheath shaped barrier devices may be formed in a variety of shapes and sizes, and include various extraneous features.

SUMMARY

A sheath shaped barrier device including an expandable feature is disclosed herein. The sheath shaped barrier device includes an elongated tube with a first end defining an enclosed tip and a second end defining an opening dimensioned to receive male genitalia. At least one sealed passage is defined along the elongated tube. A container or cavity is positioned proximal or adjacent to the second end of elongated tube and in fluid communication with the at least one sealed passage. The container includes partitioned quantities of a liquid, citric acid, and sodium bicarbonate. The container is configured to rupture or have at least one wall or partition configured to break, open or rupture upon application of a predetermined force to allow the liquid, the citric acid, and the sodium bicarbonate to mix with each other upon the application of the predetermined force.

In one embodiment, the at least one sealed passage defines a plurality of secondary passages extending longitudinally along the elongated tube towards the first end.

In another embodiment, at least one chamber is in fluid communication with the at least one sealed passage. The at least one chamber can include at least two peripheral chambers extending along a length of a majority of the elongated tube. In one embodiment, the at least one chamber includes at least one longitudinal chamber arranged at the first end of the elongated tube.

Additional embodiments are disclosed herein.

BRIEF DESCRIPTION OF THE DRAWINGS

The foregoing Summary and the following Detailed Description will be better understood when read in conjunction with the appended drawings, which illustrate a preferred embodiment of the disclosure. In the drawings.

DETAILED DESCRIPTION OF THE PREFERRED EMBODIMENTS

Figure 1A:
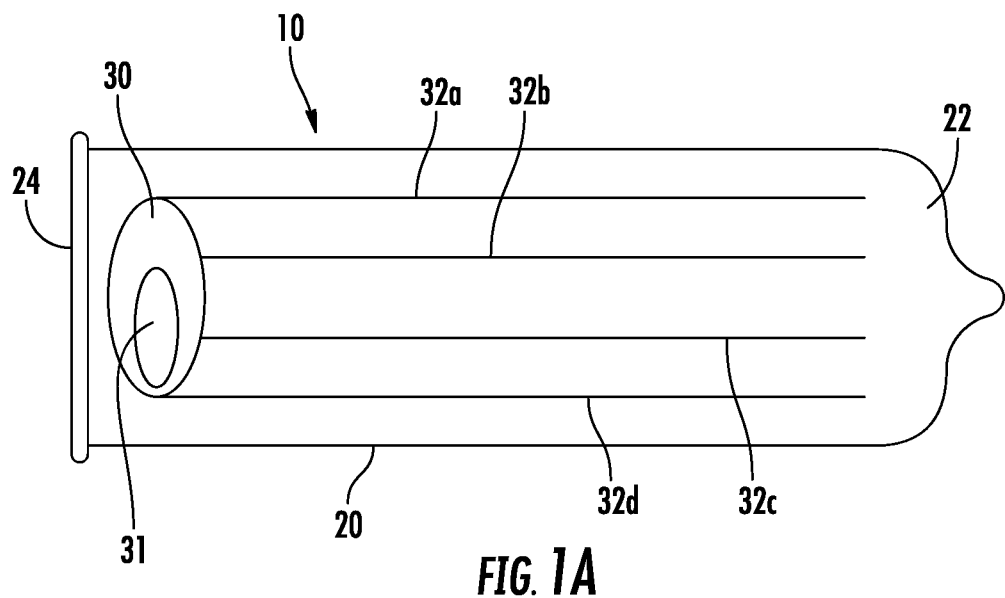
FIG. 1A is a schematic illustration according to a first embodiment of a sheath shaped barrier device.

Certain terminology is used in the following description for convenience only and is not limiting. "Axially" refers to a direction along an axis (X) of an assembly. "Radially" refers to a direction inward and outward from the axis (X) of the assembly. "Circumferentially" refers to a direction extending along a curve or circumference of a respective element relative to the axis (X) of the assembly.

A reference to a list of items that are cited as "at least one of a, b, or c" (where a, b, and c represent the items being listed) means any single one of the items a, b, or c, or combinations thereof. The terminology includes the words specifically noted above, derivatives thereof and words of similar import.

A sheath shaped barrier device 10, 110 is disclosed herein and illustrated in FIGS. 1A, 1B, 2A, and 2B. The sheath shaped barrier device 10, 110 includes an elongated tube 20, 120 with a first end 22, 122 defining an enclosed tip and a second end 24, 124 defining an opening dimensioned to receive male genitalia. The second end 24, 124 can include an elastic band, such as is normally found on a condom. At least one sealed passage 32a-32d, 132a-132f is defined along the elongated tube 20, 120.

A container 30, 130 is positioned proximal to the second end 24, 124 of the elongated tube 20, 120 and is in fluid communication with the at least one sealed passage 32a-32d, 132a-132f. The container 30, 130 is shown in the drawings as being slightly spaced away from the second end 24, 124 of the elongated tube 20, 120. One of ordinary skill in the art would understand based on the present disclosure that the container 30, 130 may be provided directly at the second end 24, 124, or along any other position of the elongated tube 20, 120. In one aspect, the container 30, 130 is formed as a thin-walled plastic container. As used herein, the term "thin" as used with respect to the walls of the containers means a thickness of 0.1 mm-1.0 mm.

The container 30, 130 includes partitioned or separated quantities of a liquid, citric acid, and sodium bicarbonate. In one embodiment, individual cartridges or containers for the liquid, citric acid, and sodium bicarbonate can be provided. In other embodiments, a single container or cartridge can be provided that includes partitions between the liquid, citric acid, and sodium bicarbonate. One of ordinary skill in the art would understand that other combinations of materials can be included in the container 30, 130. One of ordinary skill in the art would understand that other suitable combinations of a base and an acid can be selected. The combination of materials are configured to expand upon mixing with each other. One skilled in the art would understand based on the present disclosure and embodiments that any type of expansive material or gas may be integrated into the device, including compounds or materials that do not require mixing of other materials. In one aspect, any combination of materials can be used that are chemically configured to produce expansive gas. In one aspect, mixture of the materials in the container 30, 130 is configured to produce an expansive gas byproduct.

The container 30, 130 is configured to rupture upon application of a predetermined force to allow the liquid, the citric acid, and the sodium bicarbonate to mix with each other upon the application of the predetermined force. The predetermined force is preferably less than 50 newtons (N), and is more preferably less than 30 N. In one embodiment, the predetermined force generally corresponds to the amount of force capable of being applied by a person's finger(s) or palm.

In one embodiment, the container 30, 130 includes indicia 31, 131 for a user to identify where to apply the predetermined force. In one aspect, expansion of the device is configured to occur based on movement of the couple or interaction by the couple using the device. For example, movement or forces of the couple during intercourse can be configured to trigger expansion or actuation of the device.

As shown in FIGS. 1A, 1B, 2A and 2B, the at least one sealed passage 32a-32d, 132a-132f defines a plurality of secondary passages extending longitudinally along the elongated tube 20, 120 towards the first end 22, 122.

Figure 1B:
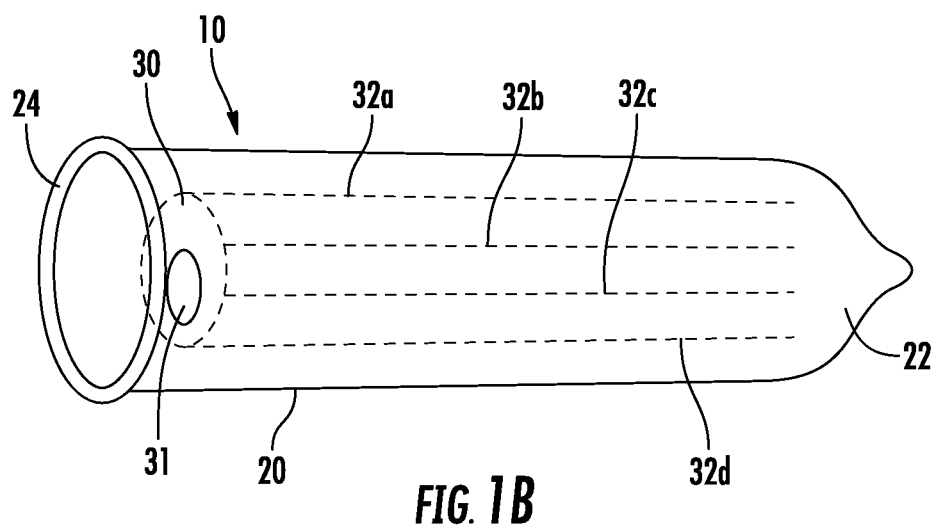
FIG. 1B is a perspective view of the device of FIG. 1A.

As shown in FIGS. 1A and 1B, the plurality of secondary passages 32a-32d are spaced circumferentially from each other around an entire circumference of the elongated tube 20. The passages 32a-32d are each independently connected at one end to the container 30. One of ordinary skill in the art would understand that the passages 32a-32d can be interconnected to each other. The opposite ends of the passages 32a-32d terminate proximal to the first end 22 of the elongated tube 20. Although four passages 32a-32d are shown in FIGS. 1A and 1B, an additional four or more passages can be provided which are not visible in FIGS. 1A and 1B. In some aspects, more or fewer passages can be provided than are illustrated.

Figure 2A:
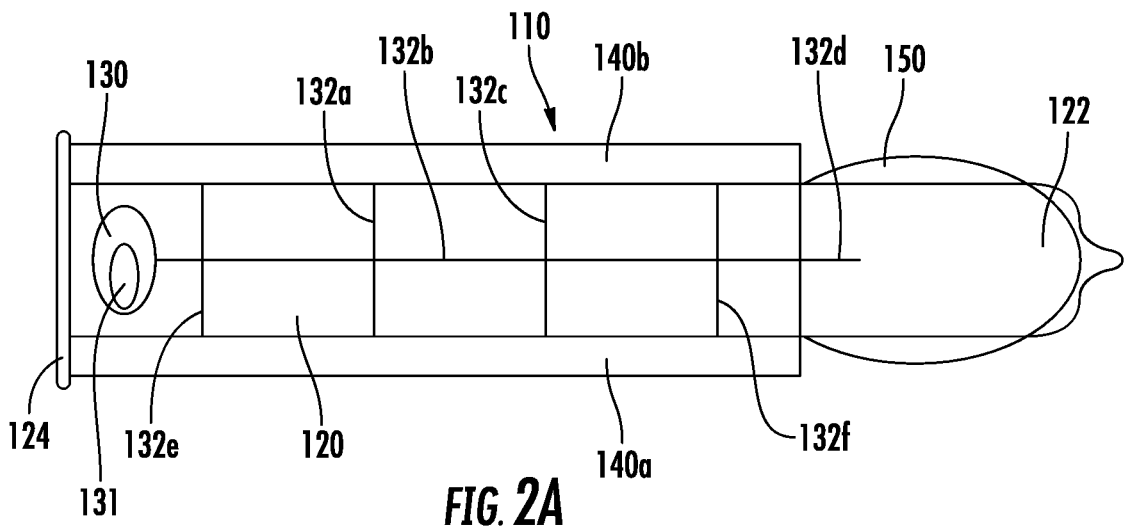
FIG. 2A is a schematic illustration according to a second embodiment of a sheath shaped barrier device.
Figure 2B:
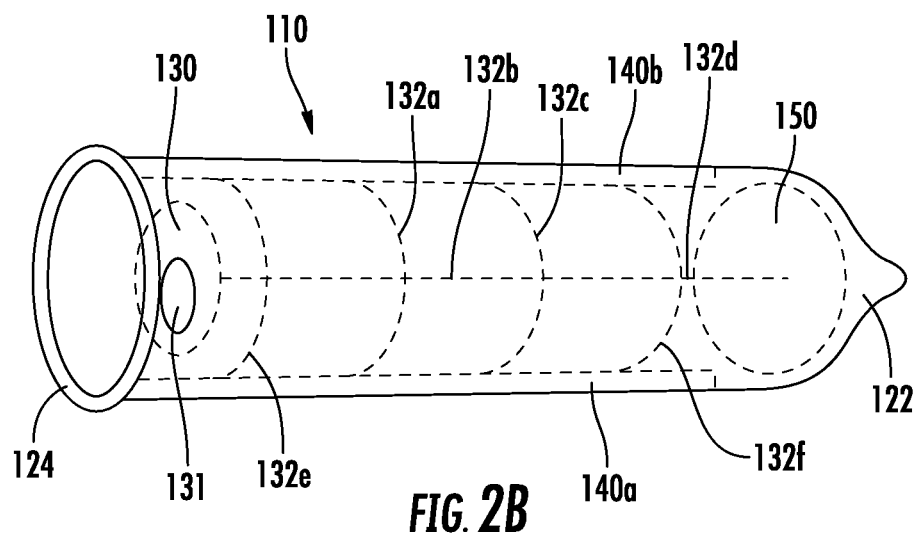
FIG. 2B is a perspective view of the device of FIG. 2A.

As shown in FIGS. 2A and 2B, at least one chamber 140a, 140b, 150 is in fluid communication with the at least one sealed passage 132a-132f. The at least one chamber includes at least two peripheral chambers 140a, 140b extending along a length of a majority of the elongated tube 120. The peripheral chambers 140a, 140b increase the girth of the device 110.

The at least one sealed passage 132a-132f can include a plurality of laterally extending passages that are spaced away from each other in an axial direction. The sealed passages 132a-132f can define a network of passages that encompass a majority of the device 110.

The at least one chamber includes at least one longitudinal chamber 150 arranged at the first end 122 of the elongated tube 120. The longitudinal chamber 150 increases the length of the device 110. In one embodiment, the longitudinal chamber 150 can be positioned along an outermost 25% of an axial or longitudinal extent of the device 120.

Each of the chambers 140a, 140b, 150 are generally configured to fill or expand upon rupturing of the container 130, which releases expansive gas into the chambers 140a, 140b, 150.

Figure 3:
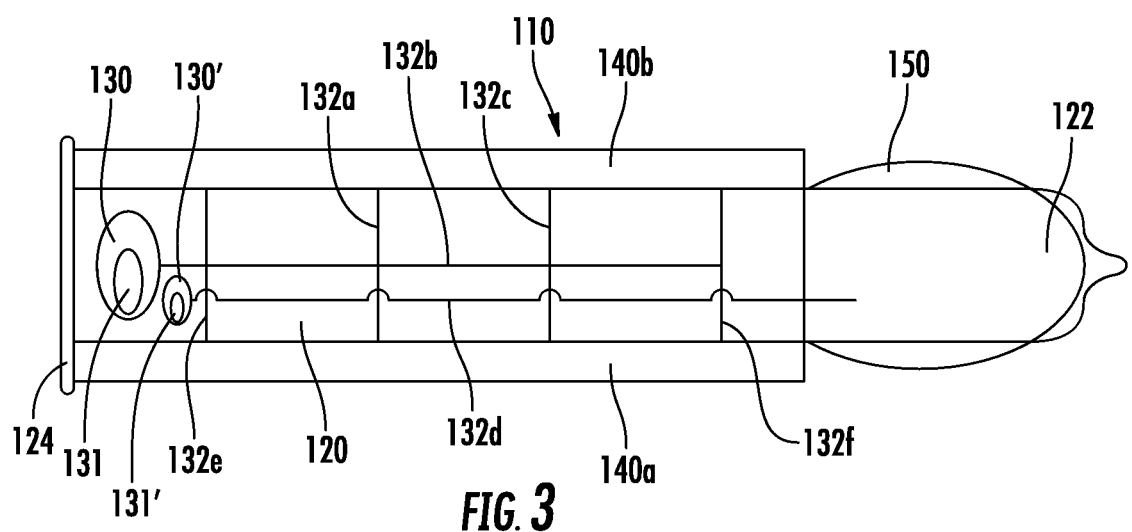
FIG. 3 illustrates another schematic illustration according to a third embodiment of a sheath shaped barrier device.

As shown in FIG. 3, in one aspect, multiple containers 130, 130' can be provided on the device that allow for selectively actuating certain chambers on the device. For example, in one aspect, a first container 130 can be provided in communication with only chambers 140a and 140b, while another second container 130' can be provided in communication with only chamber 150. As shown in FIG. 3, the passages 132a, 132b, 132c, 132f connected to container 130 all feed into chambers 140a, 140b. Passage 132d, which is connected to the second container 130' only feeds to chamber 150. In this way, the user can selectively increase only the length of the device or only the girth of the device.

The chambers disclosed herein can provide for the ability to expand in any direction, such as the radial direction, the axial direction, or any other direction. In one aspect, the chambers are arranged in a radially inward direction relative to the elongated tube. In another aspect, the chambers are arranged in a radially outward direction relative to the elongated tube. The chambers can be arranged in at least one of an axially outer direction, axially inner direction, radially inner direction, or radially outer direction. One of ordinary skill in the art would understand the basic arrangement of an expandable chamber or passage integrated into a personal sheath shaped barrier device are possible. The exact configuration of the chambers, passages, containers, and other elements of the device can be modified.

FIGS. 1 and 2 are schematics for the devices, and one skilled in the art would understand that additional features of the devices may be present but not specifically illustrated. For example, additional passages or chambers may be integrated within the devices that are not specifically illustrated in the Figures.

Having thus described the present disclosure in detail, it is to be appreciated and will be apparent to those skilled in the art that many physical changes, only a few of which are exemplified in the detailed description of the invention, could be made without altering the inventive concepts and principles embodied therein.

It is also to be appreciated that numerous embodiments incorporating only part of the preferred embodiment are possible which do not alter, with respect to those parts, the inventive concepts and principles embodied therein.

The present embodiment and optional configurations are therefore to be considered in all respects as exemplary and/or illustrative and not restrictive, the scope of the embodiments being indicated by the appended claims rather than by the foregoing description, and all alternate embodiments and changes to this embodiment which come within the meaning and range of equivalency of said claims are therefore to be embraced therein.

What is claimed is:

1. A sheath shaped barrier device for providing increased girth and length to male genitalia received within the sheath shaped barrier device, the sheath shaped barrier device comprising:

an elongated tube comprising a first end defining an enclosed tip and a second end defining an opening dimensioned to receive male genitalia;

a first peripheral chamber extending along a length of the elongated tube;

a longitudinal chamber positioned adjacent the enclosed tip;

a first sealed passage defined along the elongated tube and a second sealed passage defined along the elongated tube, the first sealed passage in fluid communication with the first peripheral chamber, and the second sealed passage in fluid communication with the longitudinal chamber; and a first container positioned proximal to the second end of the elongated tube and in fluid communication with one of the first sealed passage or the second sealed passage, the first container including partitioned quantities of at least two different materials, and the first container being configured to rupture upon application of a predetermined force to allow the at least two different materials to mix with each other upon the application of the predetermined force such that a mixture of the at least two different materials produces a gas configured to provide an expansion force;

wherein gas passing through the first sealed passage and entering the first peripheral chamber is configured to provide an expansion force to increase a girth of the first peripheral chamber, and wherein gas passing through the second sealed passage and entering the longitudinal chamber is configured to provide an expansion force to increase a length of the longitudinal chamber;

wherein the first container is in fluid communication with the first sealed passage, and further comprising a second container positioned proximal to the second end of the elongated tube and in fluid communication with the second sealed passage;

the second container including partitioned quantities of at least two different materials; and the second container being configured to rupture upon application of a predetermined force to allow the at least two different materials to mix with each other upon the application of the predetermined force such that a mixture of the at least two different materials produces a gas that provides an expansion force;

wherein gas produced in the first container is configured to pass through the first sealed passage and enter the first peripheral chamber to thereby provide an expansion force to increase a girth of the first peripheral chamber;

wherein gas produced in the second container is configured to pass through the second sealed passage and enter the longitudinal chamber to thereby provide an expansion force to increase a length of the longitudinal chamber; and wherein the first sealed passage and the second sealed passage are fluidically isolated from each other;

whereby either the girth of the first peripheral chamber or the length of the longitudinal chamber, or both, can be selectively increased.

2. The device according to claim 1, further comprising a second peripheral chamber, the second peripheral chamber in fluid communication with the first container via the first sealed passage, whereby a girth of the device is increased by expansion of the first and second peripheral chambers.

3. The sheath shaped barrier device according to claim 2, wherein the second peripheral chamber is arranged along a majority of a longitudinal extent of the elongated tube.

4. The device according to claim 3, wherein the predetermined force is less than 30 N.

5. The device according to claim 1, wherein the first sealed passage defines a plurality of secondary passages extending longitudinally along the elongated tube towards the first end.

6. The device according to claim 5, wherein the plurality of secondary passages are spaced circumferentially from each other around an entire circumference of the elongated tube.

7. The device according to claim 1, wherein the at least two different materials includes liquid, citric acid, and sodium bicarbonate.

8. The device according to claim 1, wherein the first peripheral chamber extends along a length of a majority of the elongated tube.

9. The device according to claim 1, wherein the predetermined force is less than 30 N.

10. The device according to claim 1, wherein the first container includes indicia illustrating a location for applying the predetermined force.

11. The device according to claim 1, wherein the first container is a thin-walled plastic container.

12. The device according to claim 1, wherein the device is configured to increase in both girth and length when the first container and second container are ruptured.

* * * * *